(12) United States Patent
Weingärtner et al.

(10) Patent No.: US 11,564,608 B2
(45) Date of Patent: Jan. 31, 2023

(54) SYSTEMS AND METHODS FOR ONLINE SPIKE RECOVERY FOR HIGH-DENSITY ELECTRODE RECORDINGS USING CONVOLUTIONAL COMPRESSED SENSING

(71) Applicant: The Board of Trustees of the Leland Stanford Junior University, Stanford, CA (US)

(72) Inventors: Sebastian Weingärtner, Stanford, CA (US); Tirin Moore, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 372 days.

(21) Appl. No.: 16/813,579

(22) Filed: Mar. 9, 2020

(65) Prior Publication Data
US 2020/0289011 A1 Sep. 17, 2020

Related U.S. Application Data

(60) Provisional application No. 62/816,783, filed on Mar. 11, 2019.

(51) Int. Cl.
*A61B 5/291* (2021.01)
*A61B 5/05* (2021.01)

(52) U.S. Cl.
CPC .............. *A61B 5/291* (2021.01); *A61B 5/05* (2013.01)

(58) Field of Classification Search
None
See application file for complete search history.

(56) References Cited

U.S. PATENT DOCUMENTS

| | | | |
|---|---|---|---|
| 7,834,795 B1 * | 11/2010 | Dudgeon | G06K 9/6289 |
| | | | 702/196 |
| 7,957,793 B2 | 6/2011 | Montgomery et al. | |
| 2008/0077039 A1 * | 3/2008 | Donnett | A61B 5/0006 |
| | | | 600/544 |
| 2009/0124919 A1 | 5/2009 | Ginosar et al. | |
| (Continued) | | | |

OTHER PUBLICATIONS

Akcakaya et al., "Accelerated Isotropic Submillimeter Whole-Heart Coronary MRI: Compressed Sensing Versus Parallel Imaging", Magnetic Resonance in Medicine, vol. 71, No. 2, 2014, pp. 815-822.
(Continued)

*Primary Examiner* — Jas A Sanghera
(74) *Attorney, Agent, or Firm* — KPPB LLP

(57) ABSTRACT

Systems and methods for performing online spike recovery from multi-channel electrophysiological recordings in accordance with various embodiments of the invention are described. One embodiment of a method of performing online spike recovery from multi-channel electrophysiological recordings includes: determining a set of waveform templates; continuously obtaining multi-channel electrophysiological recordings using a multi-channel electrode; and automatically performing online spike recovery from the multi-channel electrophysiological recordings using a processing system that performs a method for sparse signal recovery that continuously adjusts a processing buffer size based upon newly obtained multi-channel electrophysiological recordings.

26 Claims, 7 Drawing Sheets

(56) References Cited

U.S. PATENT DOCUMENTS

| | | | |
|---|---|---|---|
| 2014/0330761 A1* | 11/2014 | Kim | G06N 3/063 706/25 |
| 2016/0045120 A1 | 2/2016 | Friedman et al. | |
| 2016/0278713 A1* | 9/2016 | Shoaran | A61B 5/7232 |
| 2016/0331973 A1* | 11/2016 | Wheeler | A61N 1/36139 |
| 2017/0337473 A1 | 11/2017 | Bernert et al. | |

OTHER PUBLICATIONS

Asif et al., "Sparse recovery of streaming signals using 1-homotopy", IEEE Transactions on Signal Processing, vol. 62, No. 16, 2014, pp. 4209-4223.

Candes, "Compressive Sampling", Proceedings of the International Congress of Mathematicians, Madrid, Spain, 2006, 20 pgs.

Candes et al., "Stable Signal Recovery from Incomplete and Inaccurate Measurements", Communications on Pure and Applied Mathematics, vol. 59, No. 8, 2006, pp. 1207-1223.

Chaudhary et al., "Brain-computer interfaces for communication and rehabilitation", Nature Reviews Neurology, vol. 12, No. 9, 2016, p. 513.

Demko et al., "Decay Rates for Inverses of Band Matrices", Mathematics of Computation, vol. 43, No. 168, 1984, pp. 491-499.

Donoho, "Compressed Sensing", IEEE Transactions on Information Theory, vol. 52, No. 4, 2006, pp. 1289-1306.

Duarte et al., "Single-Pixel Imaging via Compressive Sampling", IEEE Signal Processing Magazine, vol. 25, No. 2, Mar. 2008, pp. 83-91.

Ekanadham et al., "A unified framework and method for automatic neural spike identification", Journal of neuroscience methods, vol. 222, 2014, pp. 47-55.

Ekanadham et al., "Recovery of sparse translation-invariant signals with continuous basis pursuit", IEEE Transactions on Signal Processing, vol. 59, No. 10, 2011, pp. 4735-4744.

Franke et al., "High-density microelectrode array recordings and real-time spike sorting for closed-loop experiments: An emerging technology to study neural plasticity", Frontiers in Neural Circuits, vol. 6, Article 105, Dec. 2012, 7 pgs.

Franke et al., "An Online Spike Detection and Spike Classification Algorithm Capable of Instantaneous Resolution of Overlapping Spikes", Journal of Computational Neuroscience, 2010, vol. 29, No. 1-2, pp. 127-148.

Hilgen et al., "Unsupervised spike sorting for large-scale, high-density multielectrode arrays", Cell reports, vol. 18, No. 10, 2017, pp. 2521-2532.

Hill et al., "Quality metrics to accompany spike sorting of extracellular signals", Journal of Neuroscience, vol. 31, No. 24, 2011, pp. 8699-8705.

Hofleitner et al., "Online Homotopy Algorithm for a Generalization of the Lasso", IEEE Transactions on Automatic Control, vol. 58, No. 12, 2013, pp. 3175-3179.

Jun et al., "Fully integrated silicon probes for high-density recording of neural activity", Nature, vol. 551, No. 7679, 2017, pp. 232-236.

Knudson et al., "Inferring sparse representations of continuous signals with continuous orthogonal matching pursuit", Advances in Neural Information Processing Systems, 2014, pp. 1215-1223.

Lefebvre et al., "Recent progress in multi-electrode spike sorting methods", Journal of Physiology-Paris, vol. 110, No. 4, 2016, pp. 327-335.

Marre et al., "Mapping a complete neural population in the retina", Journal of Neuroscience, vol. 32, No. 43, 2012, pp. 14859-14873.

Needell et al., "CoSaMP: Iterative Signal Recovery from Incomplete and Inaccurate Samples", Applied and Computational Harmonic Analysis, vol. 26, No. 3, 2009, pp. 301-321.

Needell et al., "Greedy signal recovery review", Signals, Systems and Computers, 2008 42nd Asilomar Conference on, IEEE, 2008, pp. 1048-1050.

Pachitariu et al., "Drift correction for electrophysiology and two-photon calcium imaging", Computational and Systems Neuroscience, 2018, pp. III-82, https://doi.org/10.25378/janelia.5946574.v1.

Pachitariu et al., "Fast and accurate spike sorting of high-channel count probes with kilosort", Advances in Neural Information Processing Systems, 2016, pp. 4448-4456.

Santhanam et al., "A high-performance brain-computer interface", Nature, vol. 442, No. 7099, 2006, pp. 195-198.

Sitaram et al., "Closed-loop brain training: The science of neurofeedback", Nature Reviews Neuroscience, vol. 18, No. 2, 2017, pp. 86-100.

Steinmetz et al., "Challenges and opportunities for large-scale electrophysiology with neuropixels probes", Current Opinion in Neurobiology, vol. 50, 2018, pp. 92-100.

Szlam et al., "Convolutional matching pursuit and dictionary training", arXiv.org, Retrieved from: https://arxiv.org/pdf/1010.0422.pdf, Oct. 3, 2010, 7 pgs.

Tropp, "Greed is Good: Algorithmic Results for Sparse Approximation", IEEE Transactions on Information Theory, vol. 50, No. 10, 2004, pp. 2231-2242.

Weingärtner, "Robust Online Spike Recovery for High Density Electrode Recordings using Convolutional Compressed Sensing", London, 2018, 62 pgs.

Weingärtner et al., "Robust Online Spike Recovery for High-Density Electrode Recording using Convolutional Compressed Sensing", 32nd Conference on Neural Information Processing Systems, Montreal, Canada, 2018, 6 pgs.

Yger et al., "A spike sorting toolbox for up to thousands of electrodes validated with ground truth recordings in vitro and in vivo", eLife, vol. 7, 2018, e34518, 23 pgs.

Zhang et al., "A Closed-Loop Compressive-Sending-Based Neural Recording System", Journal of Neural Engineering, vol. 12, No. 3, Apr. 2015, 17 pgs.

Zhang et al., "Communication Channel Analysis and Real Time Compressed Sensing for High Density Neural Recording Devices", IEEE Transactions on Circuits and Systems I: Regular Papers, vol. 63., No. 5, 2016, pp. 599-608.

Zhang et al., "Real-Time Compressive Sensing for Small Low Power Sensors: Maximizing System Performance in Power Impoverished Environments", Dissertation, The John Hopkins University, Baltimore, Maryland, Jul. 2016, 211 pgs.

* cited by examiner

SYSTEMS AND METHODS FOR ONLINE SPIKE RECOVERY FOR HIGH-DENSITY ELECTRODE RECORDINGS USING CONVOLUTIONAL COMPRESSED SENSING

CROSS-REFERENCE TO RELATED APPLICATIONS

The present invention claims priority to U.S. Provisional Patent Application Ser. No. 62/816,783 entitled "Systems and Methods for Online Spike Recovery for High-Density Electrode Recordings using Convolutional Compressed Sensing", filed Mar. 11, 2019, the disclosure of which is incorporated herein by reference in its entirety.

STATEMENT OF FEDERALLY SPONSORED RESEARCH

This invention was made with support by the National Institute of Health National Eye Institute grant number EY014924.

FIELD OF THE INVENTION

The present invention generally relates to multi-channel electrophysiological recording systems and more specifically to systems and methods for performing online spike recovery from multi-channel electrophysiological recordings using sparse signal recovery.

BACKGROUND

Electrophysiology remains one of the leading modalities for basic neuroscience, and has been instrumental for much of our current understanding of functioning neural circuits, particularly in behaving animals. In recent years, advancement in hardware engineering introduced technologies for electrophysiology that increased the channel count by at least an order of magnitude and unlocked simultaneous recordings from several hundreds of neurons at single cell resolution. A multi-channel electrophysiological recording system and the electrophysiological recordings obtained by it are conceptually illustrated in FIG. 1. As can readily be appreciated, the multi-channel electrophysiological recording system can obtain recordings from hundreds of neurons simultaneously. Analysis of the recordings is complicated by the tendency for signals generated by individual neurons to be recorded on multiple channels due to the dense contact spacing in the recording system. Much of the current post-processing of these types of electrophysiological recordings involves manual interaction, may be unsuitable for high channel counts or closely spaced electrode contacts, and may suffer from lengthy computational times.

At present, the viability of brain-machine-interfaces and/or closed-loop neuroscience experiments using high-density electrode arrays is hampered by the lack of efficient methods to extract spiking activity in an online fashion. Conventionally, spike sorting is performed by clustering identified spikes. This approach, however, is commonly limited to the detection of isolated spiking activity, without the capability to resolve overlapping spikes. With the introduction of high-density electrodes with increased spatial footprint the occurrence of temporally overlapping spiking activity is increasingly prevalent. Additionally, processing complexity often scales with the number of neurons and/or electrode counts and can lead to prohibitively long post-processing times in non-optimized algorithms.

SUMMARY OF THE INVENTION

Systems and methods in accordance with various embodiments of the invention perform online spike recovery in the context of high density electrode arrays. Neuronal spiking activity can be described as a sparse signal, with few scattered temporal events. Therefore, systems and methods in accordance with various embodiments of the invention employ sparse signal recovery to analyze temporal coupling between events in online streamed data. In several embodiments, results on banded matrices are used to perform spike recovery in an online setting. In many embodiments, the concept of effective bandwidth is used to derive improved bounds to minimize the buffer time and limit the computational effort required to analyze the recordings. In several embodiments, a process is utilized to determine bounds and achieve an efficient method suitable for online processing.

One embodiment of the method of the invention includes: determining a set of waveform templates; continuously obtaining multi-channel electrophysiological recordings using a multi-channel electrode; and automatically performing online spike recovery from the multi-channel electrophysiological recordings to identify spike activity using a processing system that performs a method for sparse signal recovery that continuously adjusts a processing buffer size based upon newly obtained multi-channel electrophysiological recordings.

In a further embodiment, the waveform templates are determined using offline waveform extraction from a set of training data.

In another embodiment, the waveform templates are updated over time.

In a still further embodiment, the processing system outputs information identifying spike activity detected by the processing system during the online spike recovery.

In still another embodiment, the information describing the identified spike activity comprises temporal and spatial location information.

A yet further embodiment further includes generating control signals for a stimulus provided to a subject monitored by the multi-channel electrode in response to the identified spiking activity using the processing system.

Yet another embodiment includes generating control signals for a device in response to the identified spiking activity using the processing system.

In a further embodiment again, the processing system adjusts the buffer size based upon an effective bandwidth determination.

In another embodiment again, the method for sparse signal recovery performed by the processing system is a Compressive Sampling Matching Pursuit (CoSaMP) process.

In a further additional embodiment, the processing system adds new components to the processing buffer when new multi-channel electrophysiological recordings are obtained.

In another additional embodiment, the processing system maintains an uncertainty vector for each component in the processing buffer and when, for a sequence of components of the processing buffer, the magnitude plus uncertainty is smaller than the magnitude of a component selected as a spike event minus the selected component's uncertainty, the processing system removes the sequence of components from the processing buffer and reduces the size of the processing buffer.

In a still yet further embodiment, automatically performing online spike recovery from the multi-channel electrophysiological recordings to identify spiking activity using the processing system further includes: buffering an initial component set including at least one putative spike event in the processing buffer; receiving new multi-channel electrophysiological recordings and adding at least one new component to the processing buffer; estimating uncertainty for components in the initial component set stored in the processing buffer including the at least one putative spike event; removing from the processing buffer components of the buffered initial component set occurring prior to a putative spike event, when the estimated uncertainty of each of the components prior to the putative spike event is less than an uncertainty threshold; and decreasing the buffer length of the processing buffer based upon the components removed from the buffer.

In still yet another embodiment, the multi-channel electrode comprises at least 32 channels.

A still further embodiment again, includes: a probe capable of capturing multi-channel electrophysiological recordings; and a processor system. In addition, the processor system is configured by a software application to: determine a set of waveform templates; obtain new multi-channel electrophysiological recordings using the probe; and perform online spike recovery by identifying spike events using the components in the processing buffer. Furthermore, when new multi-channel electrophysiological recordings are obtained the software configures the processor system to: add at least one new component to a processing buffer, where the at least one new component is determined using the waveform templates; and adjust the processing buffer size.

In still another embodiment again, the processor system is further configured by the software to determine the waveform templates using offline waveform extraction from a set of training data.

In a still further additional embodiment, the processor system is further configured by the software to update the waveform templates over time.

In still another additional embodiment, the processor system is further configured by the software to output information describing the identified spiking activity.

In a yet further embodiment again, the information describing the identified spiking activity comprises temporal and spatial location information.

Yet another embodiment again further includes an output interface. In addition, the processor system is further configured by the software to control a device in response to the identified spiking activity via the output interface.

A yet further additional embodiment also includes an output interface. In addition, the processor system is further configured by the software to control stimuli provided to a subject monitored by the probe in response to the identified spiking activity via the output interface.

Yet another additional embodiment further includes an analog-to-digital converter configured to receive signals from the probe and store data in a memory of the processor system.

In a still yet further embodiment again, the processor system is further configured by the software to adjust the buffer size based upon an effective bandwidth determination.

In still yet another embodiment again, the processor system is further configured by the software to perform online spike recovery using a sparse signal recovery processing utilizing Compressive Sampling Matching Pursuit (CoSaMP).

In a still yet further additional embodiment, the processor system is further configured by the software to: maintain an uncertainty vector for each component in the processing buffer; and remove a sequence of components from the processing buffer and reduce the size of the processing buffer, when the sequence of components each have a magnitude plus uncertainty that is smaller than the magnitude of a component selected as a spike event minus the selected component's uncertainty.

In a yet further additional embodiment again, the processor system is further configured by the software to perform online spike recovery by: buffering an initial component set including at least one putative spike event in the processing buffer configured to have an initial buffer length; estimating uncertainty for components in the initial component set stored in the processing buffer including the at least one putative spike event; removing from the processing buffer components of the buffered initial component set occurring prior to a putative spike event, when the estimated uncertainty of each of the components prior to the putative spike event is less than an uncertainty threshold; and decreasing the buffer length of the processing buffer based upon the components removed from the buffer.

In yet another additional embodiment again, the multi-channel electrode comprises at least 32 channels.

BRIEF DESCRIPTION OF THE DRAWINGS

It should be noted that the patent or application file contains at least one drawing executed in color. Copies of this patent or patent application publication with color drawing(s) will be provided by the Office upon request and payment of the necessary fee.

DETAILED DESCRIPTION

Figure 1:
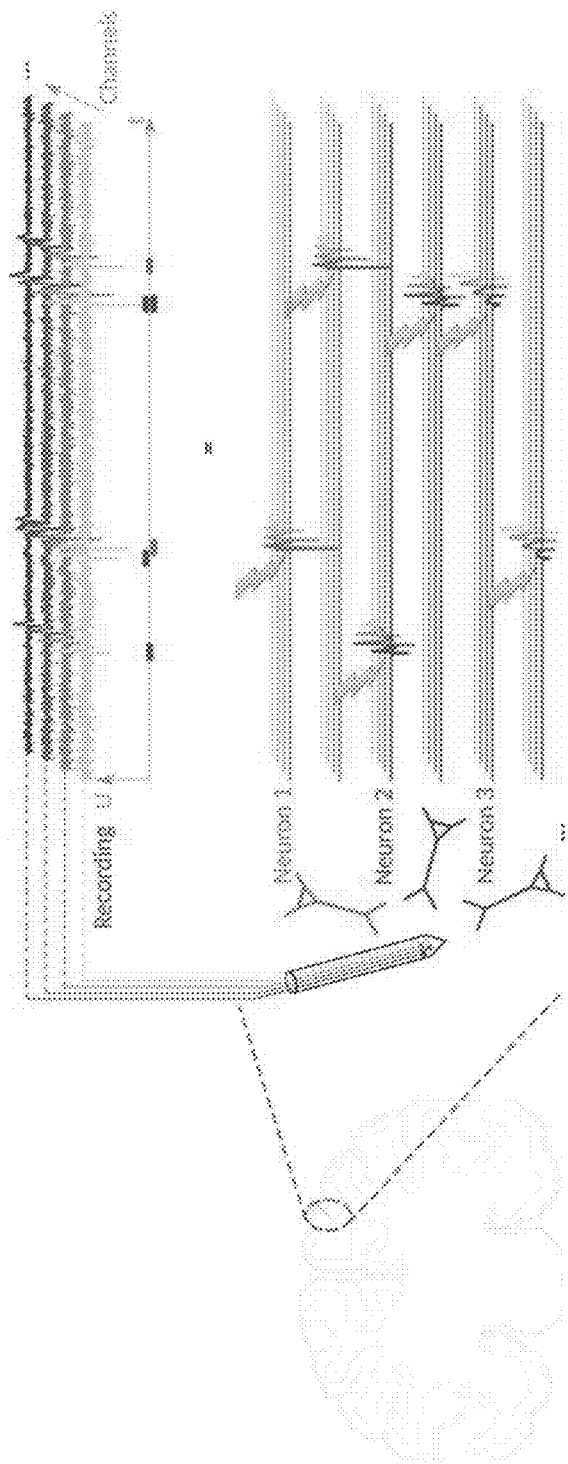
FIG. 1 conceptually illustrates a multi-channel electrophysiological recording system and the multi-channel electrophysiological recordings obtained by such a system.

Turning now to the drawings, systems and methods for performing online spike recovery from multi-channel electrophysiological recordings using sparse signal recovery in accordance with various embodiments of the invention are illustrated. In many embodiments, a linear convolutional model is used to describe the extracellular recording and compressed sensing is used to recover the spiking activity as a sparse signal. In several embodiments, error propagation in response to new measurements can be characterized using results on banded matrices. In a number of embodiments, accurate signal recovery is feasible with finite buffers in an online setting by utilizing processes that derive improved bounds for the buffer size. In many embodiments, buffer sizes are determined by introducing the concept of effective bandwidths. In several embodiments, an adaptation of a Compressive Sampling Matching Pursuit (CoSaMP) process is utilized for online processing by restricting iterations to a finite buffer. Evaluation with noisy, ground-truth simulations show virtually identical performance to offline processing indicating an appropriate choice of the buffer size. Negligible errors were also observed for signal-to-noise ratio larger than 7. Furthermore, systems and methods in accordance with a number of embodiments of the invention can achieve spike detection comparable to manual spike sorting in high-density recordings from a behaving macaque (deviation: 6.6-7.7%), while enabling resolution of overlapping activity. Accordingly, sparse signal recovery processes in accordance with various embodiments of the invention that utilize limited buffer sizes enable accurate online spike detection. In combination with offline waveform extraction from training data, this provides a means for using single-neuron spiking activity in closed loop experiments or brain-machine interfaces.

Spike sorting for high-density electrode recordings has been the topic of several recent studies. Fully automated methods for spike sorting have been proposed involving incorporation of spatial location in addition to waveform features in the clustering to achieve improved sorting performance and resolve temporal and non-spatial overlaps. A semi-automatic suite has also been proposed, where a manual curation step follows template matching based detection and clustering, enabling sorting. However, conventional systems for obtaining high-density multi-channel electrophysiological recordings do not possess the capability to perform online spike detection.

Recent efforts towards online spike detection have focused on template matching. Use of matched filters to detect activity associated with specific waveforms has been proposed. To allow for the detection of overlapping spikes, detangling of non-orthogonal filters can be performed. This technique allows for computational efficient processing, potentially suitable for hardware implementation. However, so far the method has not been effectively performed on high-density multi-electrode arrays. Furthermore, the detangling step can theoretically lead to noise amplification. To avoid the issue of noise amplification and to improve robustness, systems and methods in accordance with many embodiments of the invention employ concepts from compressed sensing to a straight-forward linear generative model.

Convolutional compressed sensing can be utilized in applications with translationally or temporally invariant signals. Accordingly, convolutional compressed sensing can be used to enable spike sorting of electrophysiology data with linear programming. Interpolational expansion of the encoding matrix can also be used to allow for continuous estimation of the event times with minor penalty on the incoherence. Spike detection can also be performed with the greedy CS method OMP and an interpolational encoding matrix, based on a singular-value-decomposition of the waveforms. Studies have demonstrated the usefulness of the sparse-linear model to describe electrophysiological recordings.

Systems and methods in accordance with a number of embodiments of the invention are concerned with the issue of both updated measurement and spike vectors, which describe the process of online signal acquisition and spike recovery. In contrast to previous work, this implies that the signal x is constantly expanded and new non-zero components are added. In a number of embodiments, the process involves obtaining an estimate of the number of non-zero components. To account for the increasing number of non-zero elements, this estimation can be obtained on a per temporal slice basis to provide homogeneous activity profiles across the recording, and avoid activity clusters, in case of changes of recording signal strength or noise-level.

In several embodiments, it is assumed that the waveform templates are known to the spike detection process, during online processing. The templates can be obtained at the beginning of the recording from offline spike sorting on several minutes worth of training data. In a number of embodiments, it might be sufficient for the process to pick up well-isolated single unit activity to form the encoding matrix. As seen in the results presented below, the online processing will still be capable of resolution of overlapping activity. However, waveform templates are known to be subject to electrode drifts and other factors inducing temporal variability. Hence, many embodiments employ additional means for updating the waveform template over time. For example, approaches from convolutional sparse coding can be applied to jointly update the encoding matrix and the estimated activity. Alternatively, motion can be modeled explicitly using cross-channel information allowing for dynamic waveform updates. In certain embodiments, the system performs a process involving a combination of online and offline spike sorting and template updates providing means for utilization of single-cell activities in online applications.

The nature of electrophysiological recordings and systems and methods for performing online spike recovery from multi-channel electrophysiological recordings using sparse signal recovery in accordance with various embodiments of the invention are discussed further below.

Systems for Performing Online Spike Recovery

Figure 2:
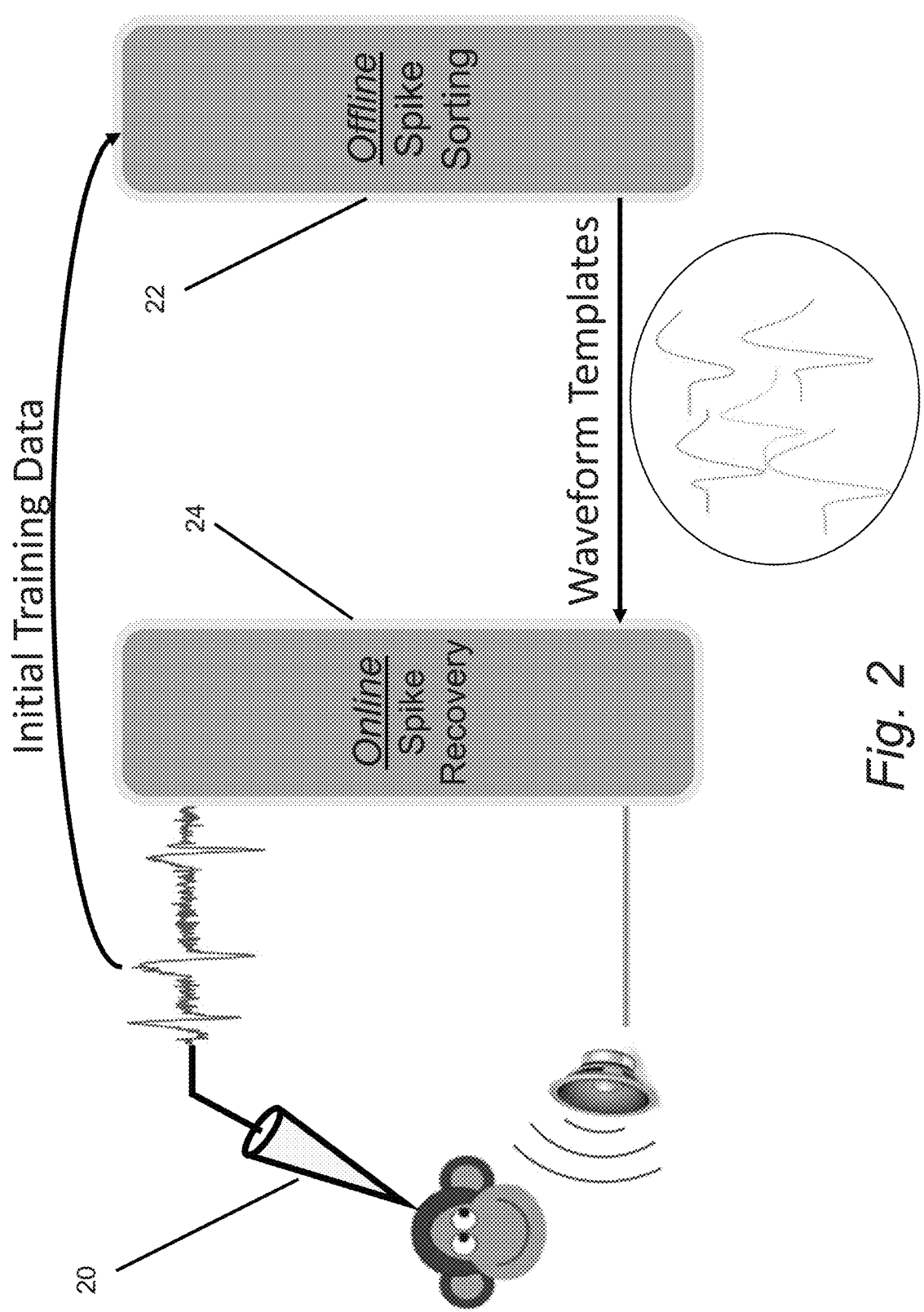
FIG. 2 conceptually illustrates a system for performing online spike recovery from multi-channel electrophysiological recordings using sparse signal recovery in accordance with an embodiment of the invention.

A system for performing online spike recovery from multi-channel electrophysiological recordings using sparse signal recovery in accordance with an embodiment of the invention is illustrated in FIG. 2. In the illustrated embodiment, stimulus is provided to a subject in which a multi-channel electrode 20 is implanted. In several embodiments, training data is collected and an offline process 22 utilized to generate a set of template waveforms. The template waveforms can then be utilized to perform an online spike detection process 24 using any of the processes described herein. In a number of embodiments, the data is recorded using a high speed analog-to-digital converter and is stored in memory of a recording system. In certain embodiments, the recording system includes a processor configured by software to implement the various processes associated with identification of the waveform templates and the performance of online spike recovery using the waveform templates. In several embodiments, the system can also include outputs that control stimuli to the subject and/or other devices such as (but not limited to) robotic manipulators to provide a brain machine interface. As can readily be appreciated the software of the recording system described herein can be configured to perform any of the processes described below for performing the offline and/or online spike recovery processes in accordance with various embodiments of the invention.

While specific systems for performing online spike recovery from multi-channel electrophysiological recordings are described above with reference to FIG. 2, any of a variety of systems for performing online spike recovery from multi-channel electrophysiological recordings including (but not limited to) conventional systems that are appropriately modified to implement processes similar to the processes described herein and/or systems that identify waveform templates via online analysis of received signals can be utilized as appropriate to the requirements of specific applications in accordance with various embodiments of the invention.

A brief overview of a linear convolutional model that can be used to describe neuronal signal recordings is provided below as a precursor to a discussion of processes for performing online spike recovery from multi-channel electrophysiological recordings using sparse signal recovery in accordance with a number of embodiments of the invention.

Linear Convolutional Models for Neuronal Signals

Figure 3:
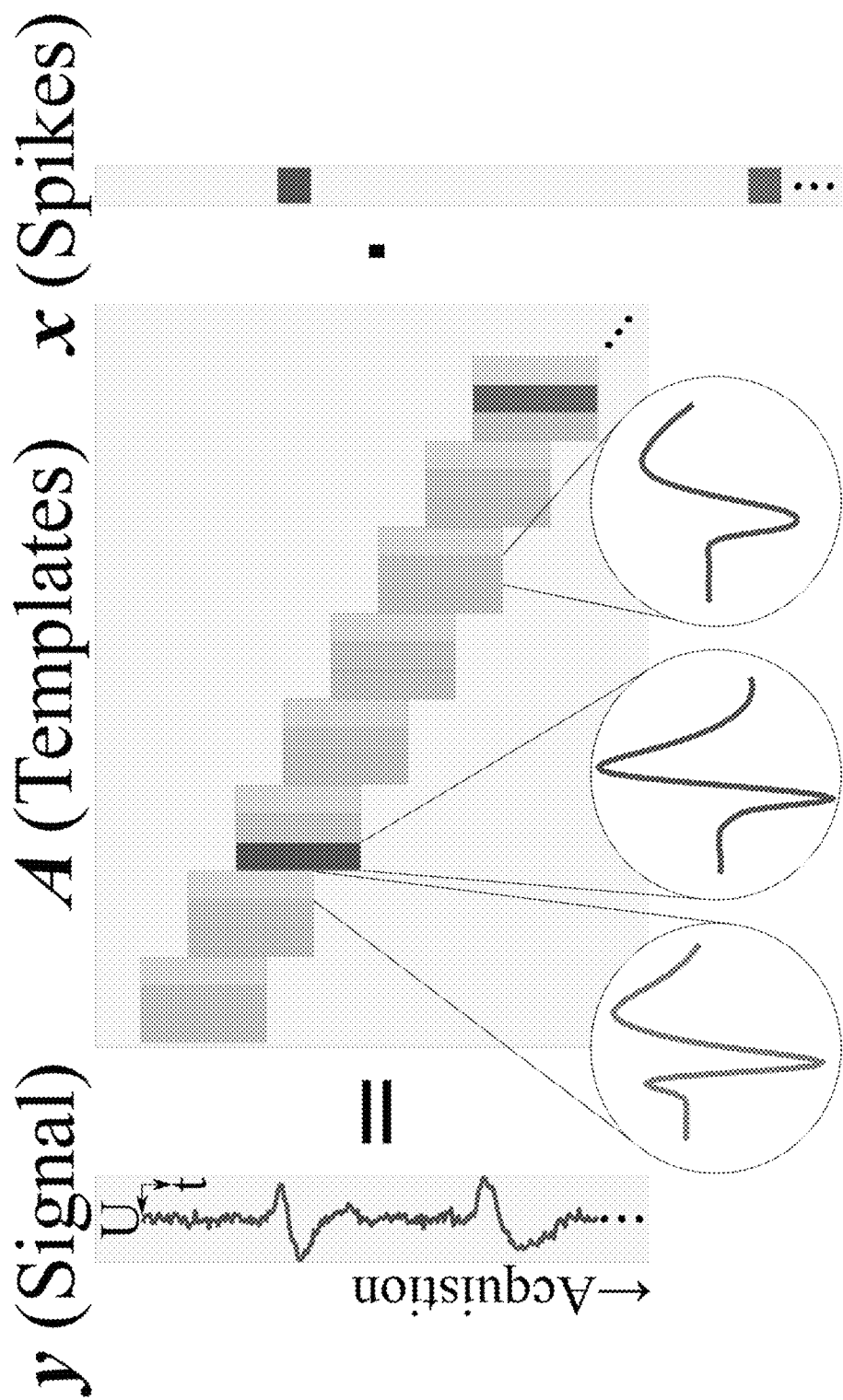
FIG. 3 conceptually illustrates the manner in which a linear convolutional model can be used to describe recordings made by extracellular electrodes as a linear combination of waveform templates corresponding to action potentials of spatially proximate cells.

Extracellular electrodes can record action potentials as emitted by spatially proximate cells. Due to the conducting nature of extracellular fluid electrical potentials can sum up linearly. These potentials are commonly assumed to be largely temporally invariant responses ("waveform templates"). In discrete time the extracellular signal $y \in \mathbb{R}^{hn}$ of n time-steps on h recording channels, can be described as a linear function of the vector of all possible spiking events $x \in \mathbb{R}^{nm}$ of a total of m neurons as $y = Ax$ with an encoding matrix $A \in \mathbb{R}^{hn \times nm}$. This linear convolutional model of electrophysiological recordings is conceptually illustrated in FIG. 3. As evidenced from the illustration of the model in FIG. 3, A has a "stacked"-convolutional structure, where each column represents a time-shifted copy of the multi-channel waveform template. This gives a Toeplitz-structure for a single neuron and a single channel. The final matrix A is obtained by interleaving the rows of these Toeplitz matrices for different channels and then interleaving the columns of the resulting matrices for different neurons. This finally yields a matrix formed of time shifted copies of the block of multi-channel waveforms. Without loss of generality it can be assumed that all waveforms and, thus, all columns $a_i$ of A have unit norm and cover $\tau$ timesteps.

Spike recovery involves the inverse problem of obtaining the spiking activity vector x from the measured signal y, when the encoding matrix A is assumed to be known. This is a common assumption for online spike recovery, where the waveforms are usually characterized before the online processing. In the context of online processing, however, not all measurement data is available at once. Instead at each time point t, h new measurements and in new possible spiking events become available. Let $y_t \in \mathbb{R}^{ht}$ describe the data available until time t, i.e. the first ht entries of y. Thus $y_t$ is equal to $y_{t-1}$ appended with the h data points acquired at time t. Correspondingly, $x_t \in \mathbb{R}^{tm}$ can be defined as the spike events of the first t time steps and the encoding matrix $A_t \in \mathbb{R}^{ht \times tm}$ as the upper-left ht×tm sub-matrix of A. For temporal sub-problems $y_t = A_t x_t$ the effect of the newly arriving measurements at time point t, can be assessed using the update vector $\Delta y_t \triangleq (0 \ldots 0 \ y_{t,(t-1)h} \ldots y_{t,th})^T \in \mathbb{R}^{ht}$ where $y_{t,(t-1)h}, \ldots, y_{t,th}$ are the last h entries of $y_t$.

Online Recovery of Sparse Signals

Compressed sensing (CS) can enable robust recovery of sparse signals from linear measurements that demonstrate a certain degree of incoherence. CS was first described by E. J. Candes in "Compressive sampling", Proceedings of the International Congress of Mathematicians, Madrid, Spain, 2006, the disclosure of which is incorporated herein by reference in its entirety. Greedy methods have been proposed for efficient sparse signal recovery, potentially allowing real-time applications. These methods iteratively determine the location of the non-zero entries of x, i.e. its support. In the online processing formulation, for a fixed time-point t, $\mathcal{T} \subseteq \{1, \ldots, tm\}$ can be an index set, containing candidate locations for the support of x. In addition, $A_{|\mathcal{T}}$ can be defined to be the submatrix formed by taking the columns of $A_t$ specified by $\mathcal{T}$. The current approximation to $y_t$ can be defined as $\hat{y}_t = A_{|\mathcal{T}} A_{|\mathcal{T}}^\dagger y$, and the corresponding residual as $$r_t \triangleq y_t - \hat{y}_t = (I - A_{|\mathcal{T}}(A_{|\mathcal{T}}^T A_{|\mathcal{T}})^{-1} A_{|\mathcal{T}}^T) y_t, \quad (1)$$

where I is the identity matrix. Greedy algorithms can modify the set of candidate locations for the support based on the correlation between the current residual and the columns of the encoding matrix $A_t$. These correlations are captured in $$b_t = A_t^T r_t = (A_t^T - A_t^T A_{|\mathcal{T}}(A_{|\mathcal{T}}^T A_{|\mathcal{T}})^{-1} A_{|\mathcal{T}}^T) y_t \quad (2)$$

Hence, the support determination can depend upon the magnitude of the components of $b_t$. The error propagation for a measurement update can be studied with the following Lemma describing the effect of the newly incoming data on these magnitudes as a function of their position.

Lemma 1. For a given time point t and an index set $\mathcal{T} \subset \{1, \ldots, tm\}$, let $b_t$ be the vector of projected residuals as defined in (2). Further let $$\kappa = \frac{\sigma_{max}}{\sigma_{min}}$$

the condition number of $(A_{|\mathcal{T}}^T A_{|\mathcal{T}})$ with $\sigma_{min}$, $\sigma_{max}$ being its minimal and maximum eigenvalues, respectively. For any index $j \leq (t-\tau)m$, the change in the $j^{th}$ component of $b_t$, $\Delta b_j$ for a measurement update $\Delta y = (0 \ldots 0 \ y_{(t-1)h} \ldots y_{th})^T$ is bounded by $$|\Delta b_j| \leq 2\tau^2 m^2 K \rho^{\lceil (t-2\tau)m - j \rceil} \|\Delta y\|_2 \quad (3)$$

with $$K = \max\left(\sigma_{min}^{-1}, \frac{1+\sqrt{\kappa}}{2\sigma_{max}}\right), \rho = \left(\frac{\sqrt{\kappa}-1}{\sqrt{\kappa}+1}\right)^{\frac{1}{m\tau}}.$$

Figure 4:
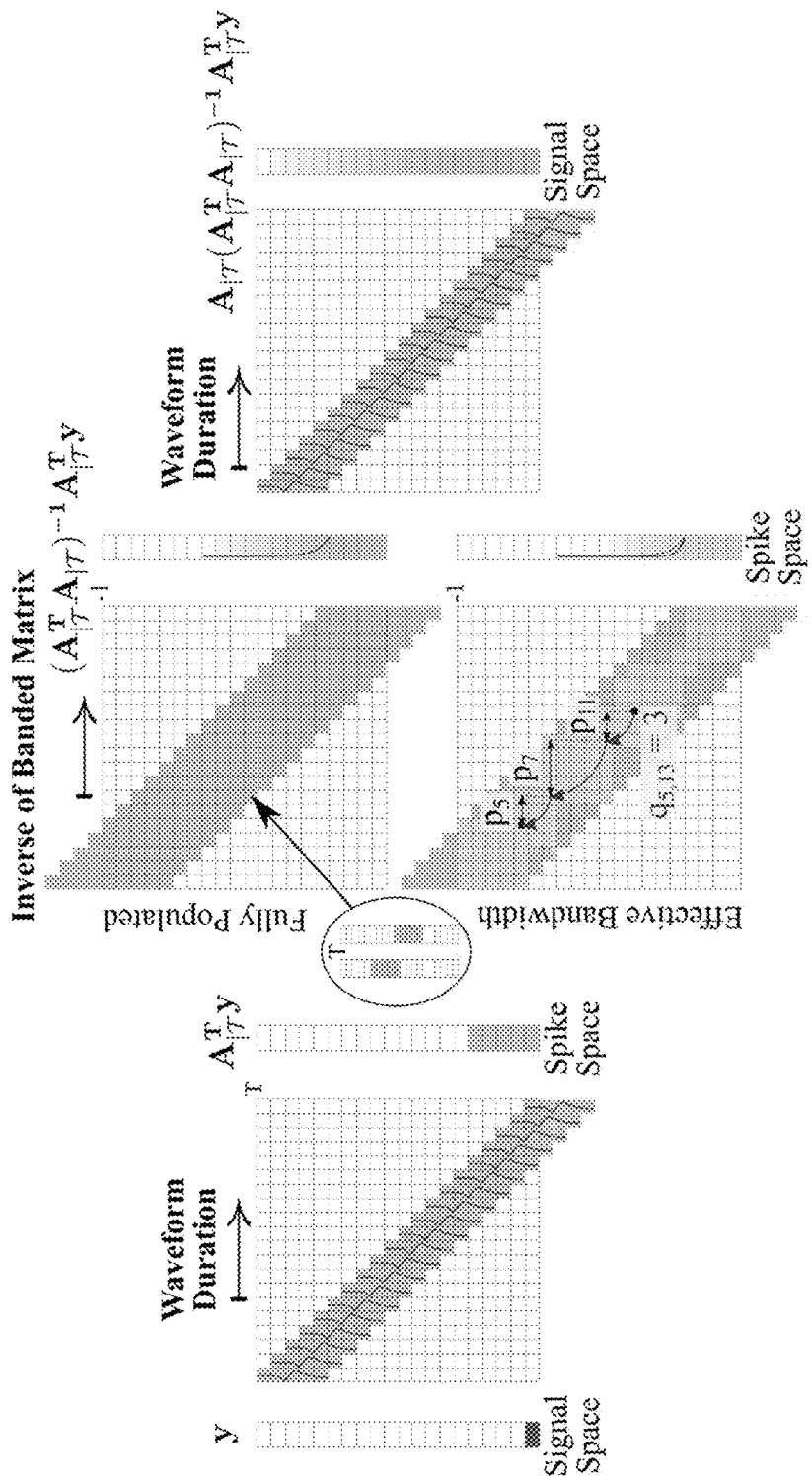
FIG. 4 conceptually illustrates error-propagation when a greedy algorithm is applied to perform spike identification.

The Lemma can be proven by decomposing (2) stepwise as illustrated in FIG. 4, and analyzing the error propagation for each term. For analysis of the inverse of the Grammian matrix $(A_{|\mathcal{T}}^T A_{|\mathcal{T}})^{-1}$, it can be stated that the Grammian matrix has banded structure and thus a result described in Demko, Stephen, William F. Moss, and Philip W. Smith. "Decay rates for inverses of band matrices." Mathematics of computation 43.168 (1984): 491-499, the disclosure of which is herein incorporated by reference in its entirety, can be applied to bound the error propagation exponentially. The bound proposed by Demko et al. is referred to as the DMS bound herein. The detailed proof is provided in U.S. Provisional Application Ser. No. 62/816,783 incorporated by reference in its entirety above.

The following Corollary follows by summing (3) over time and expressing it as a geometric sun. It shows that irrespective of the measurement time, the effect on old signal components can be considered finitely bounded, with an exponentially decaying bound.

Corollary 1. For a given index j and an interval $[\sigma_{min}, \sigma_{max}]$ chosen to contain the eigenvalue spectrum of all $A_t$ with t≥j. Let $\Delta y_t$ be a measurement update such that there is a $t_0 \geq j$ with $\Delta y_{t,i}=0$ for all components of $\Delta y_t$ at positions $i \leq t_0 m$ and $\|(\Delta y_{t,(t'm+1)} \ldots \Delta y_{t,((t'+1)m)}{}^t)\|_2 \leq z$ for $t'>t_0$. For $\Delta b_{t,j}$ defined as the $j^{th}$ component of $b_t \triangleq A_t{}^T r_t$ it holds $$\lim_{t\to\infty} |\Delta b_{t,j}| \leq \frac{2\tau^2 m^2 K}{1-\rho} \rho^{|(t_0-2\tau)m-j|} z. \quad (4)$$

Proof of Corollary 1.

$$\lim_{t\to\infty} |\Delta b_{t,j}| \leq \sum_{i=t_0}^{\infty} 2\tau^2 m^2 K \rho^{|(t-2\tau)m-j|+iz} = \quad (5)$$

$$2\tau^2 m^2 K \rho^{|(t_0-2\tau)m-j|} \sum_{i=0}^{\infty} \rho^i z = \frac{2\tau^2 m^2 K}{1-\rho} \rho^{|(t_0-2\tau)m-j|} z$$

Error Bounds for Online Sparse Spike Recovery

The off-diagonal decay for the inverse of banded matrices obtained using processes similar to those described above typically rely on bounding the error using Chebyshev approximation or other approaches assuming a fully populated banded structure. However, in the spike recovery problem, the number of overlapping spike events ultimately determines the effective bandwidth of $A_{t|T}^T A_{t|T}$. Hence, the bandwidth is much smaller than the theoretical maximum of mτ (all m neurons firing at τ consecutive time points). For example, taking the refractory period of neurons into account can yield a maximum bandwidth of 2 m. However, even within this reduced bandwidth many of the off-diagonal elements amount to zero. To better capture this, the effective bandwidth of a matrix B for position i can be defined as $$p_i(B) \triangleq (\max\{j \geq i | \exists k \leq i : |B_{k,j}|>0 \ \lor |B_{j,k}|>0\})-i. \quad (6)$$

Additionally, the minimal path length between i and j can be defined as $$q_{i,j}(B) \triangleq \min\left\{N \mid \exists (i_n)_{n\leq N} : \forall L < N, i_L = \sum_{l=1}^{L} p_{i_l}(B) \land i_N = j\right\} \quad (7)$$

with $q_{i,j}(B)=\infty$ if no such N exists.

In many embodiments, a process is used that bounds error propagation following a measurement update that improves upon the bound provided using Chebyshev approximation. The improved bound is stated in the following Theorem.

Theorem 1. For the definitions as slated in Corollary 1, and $b_{t,j}$, the $j^{th}$ component of $b_t = A_t{}^T r_t$, the error is bounded by $$|\Delta b_{t,j}| \leq \frac{(2\tau-1)\tau m^2}{\sigma_{min}(1-\sqrt[\tau m]{\eta})} \eta^{q_{j',t_0'}(A^T A)} z \quad (8)$$

with $j'=j+\tau m$, $t'_0=(t_0-t)m+1$.

To prove this Theorem, the following technical Lemma is stated and proven.

Lemma 2. For any matrix $A \in \mathbb{R}^{n \times n}$ full rank, let $B=(A^T A)^{-1}$ be the inverse of its Grammian Matrix. Let $\sigma_{min}$, $\sigma_{max}$ be the minimum and maximum eigenvalues of $A^T A$. For an off-diagonal entry $B_{i,j}$ of B, we have $$|B_{i,j}| \leq \frac{\eta^{q_{i,j}(A^T A)}}{\sigma_{min}}, \eta = (1 - \sigma_{min}/\sigma_{max}). \quad (9)$$

Note that $q_{i,j}(B)=\infty$ if and only if there is a k with i≤k≤j and $p_k(B)=0$, i.e. the encoding matrix can be fully decoupled or temporally "sliced". In this case, of no overlap, the bound yields 0.

Proof. As $A^T A$ is positive definite, any of its eigenvalues, σ satisfies $0 < \sigma_{min} \leq \sigma \leq \sigma_{max}$. Consider the matrix $C \triangleq I-(A^T A)/\sigma_{max}$. For any eigenvector v of C with corresponding eigenvalue μ it follows $$Cv = \mu v \Leftrightarrow (I - (A^T A)/\sigma_{max})v = \mu v \quad (10)$$

$$\Leftrightarrow (A^T A)v = (1-\mu)\sigma_{max} v.$$

Hence v is also an eigenvector of $A^T A$, with the corresponding eigenvalue $\sigma=(1-\mu)\sigma_{max}$. Since $0<\sigma/\sigma_{max}\leq 1$, any eigenvalue μ of C satisfies $0 \leq \mu \leq \eta \triangleq (1-\sigma_{min}/\sigma_{max}) < 1$. Specifically the spectral 2-norm of C satisfies $\|C\|_2 < 1$. Thus, the Neumann matrix series can be applied to C and yields $$B = (A^T A)^{-1} = \frac{1}{\sigma_{max}}(I-C)^{-1} = \frac{1}{\sigma_{max}}\sum_{i=0}^{\infty} C^i = \frac{1}{\sigma_{max}}\sum_{i=0}^{\infty}\left(I - \frac{A^T A}{\sigma_{max}}\right)^i \quad (11)$$

Similar to the regular bandwidth, the effective bandwidth propagates in multiplication. For square matrices G, H ∈ $\mathbb{R}^{n \times n}$, $p_i(GH) \leq p_i(G)+p_{i+p_i(G)}(H)$. Repeated application of this rule yields for l>0, i≠j that for the matrix $D \triangleq \sum_{i=0}^{l} C^i$ with $l \leq q_{i,j}(C)$, it follows $D_{i,j}=0$. Thus $$e_i^T B e_j = \frac{1}{\sigma_{max}} e_i^T \left(\sum_{i=0}^{\infty} C^i\right) e_j \quad (12)$$

$$= \frac{1}{\sigma_{max}}\left(e_i^T \left(\sum_{i=0}^{q_{i,j}(C)} C^i\right) e_j + e_i^T \left(\sum_{i=q_{i,j}(C)+1}^{\infty} C^i\right) e_j\right)$$

$$= \frac{e_i^T}{\sigma_{max}}\left(\sum_{i=q_{i,j}(C)+1}^{\infty} C^i\right) e_j = e_i^T \frac{C^{q_{i,j}(C)}}{\sigma_{max}}\left(\sum_{i=0}^{\infty} C^i\right) e_j,$$

yielding $$|B_{i,j}| \leq \|e_i^T\|\left\|\frac{C^{q_{i,j}(C)+1}}{\sigma_{max}}\left(\sum_{i=0}^{\infty} C^i\right)\right\|\|e_j\| \leq \frac{\eta^{q_{i,j}(C)+1}}{\sigma_{max}}\left(\sum_{i=0}^{\infty} \kappa^i\right) = \quad (13)$$

-continued $$\frac{\eta^{q_{i,j}(C)}}{\sigma_{max}} \frac{1}{1-\eta} = \frac{\eta^{q_{i,j}(C)}}{\sigma_{min}}$$

As C and $A^TA$ have the same off-diagonal entries, $p_i(C)=p_i(A^TA)$ for all i, and thus $q_{i,j}(C)=q_{i,j}(A^TA)$ for all i,j, which leads to the statement in the Lemma. □

Note that for the case of a fully populated $m\tau$-banded matrix B, $\forall i: p_i(C)=m\tau$ and $$q_{i,j}(B) = \left\lceil \frac{|i-j|}{m\tau} \right\rceil.$$

Further, for $$\kappa = \frac{\sigma_{max}}{\sigma_{min}}$$

it yields $$\eta = \frac{\kappa-1}{\kappa} \text{ and } \rho^{m\tau} = \frac{\sqrt{\kappa}-1}{\sqrt{\kappa}+1} = \frac{\kappa-1}{\kappa+2\sqrt{\kappa}+1}.$$

Hence, (13) yields asymptotically comparable bounds for the fully populated case. However, if the effective bandwidth is locally lower, (13) decays more quickly than previous bounds. This more restrictive bound facilitates the use of shorter buffer windows, and therefore enables faster processing in the online setting than conventional processing techniques. Use of the new bounds described above in processes that perform online spike recovery from multi-channel electrophysiological recordings in accordance with various embodiments of the invention are discussed further below.

Online CoSaMP

Figure 5:
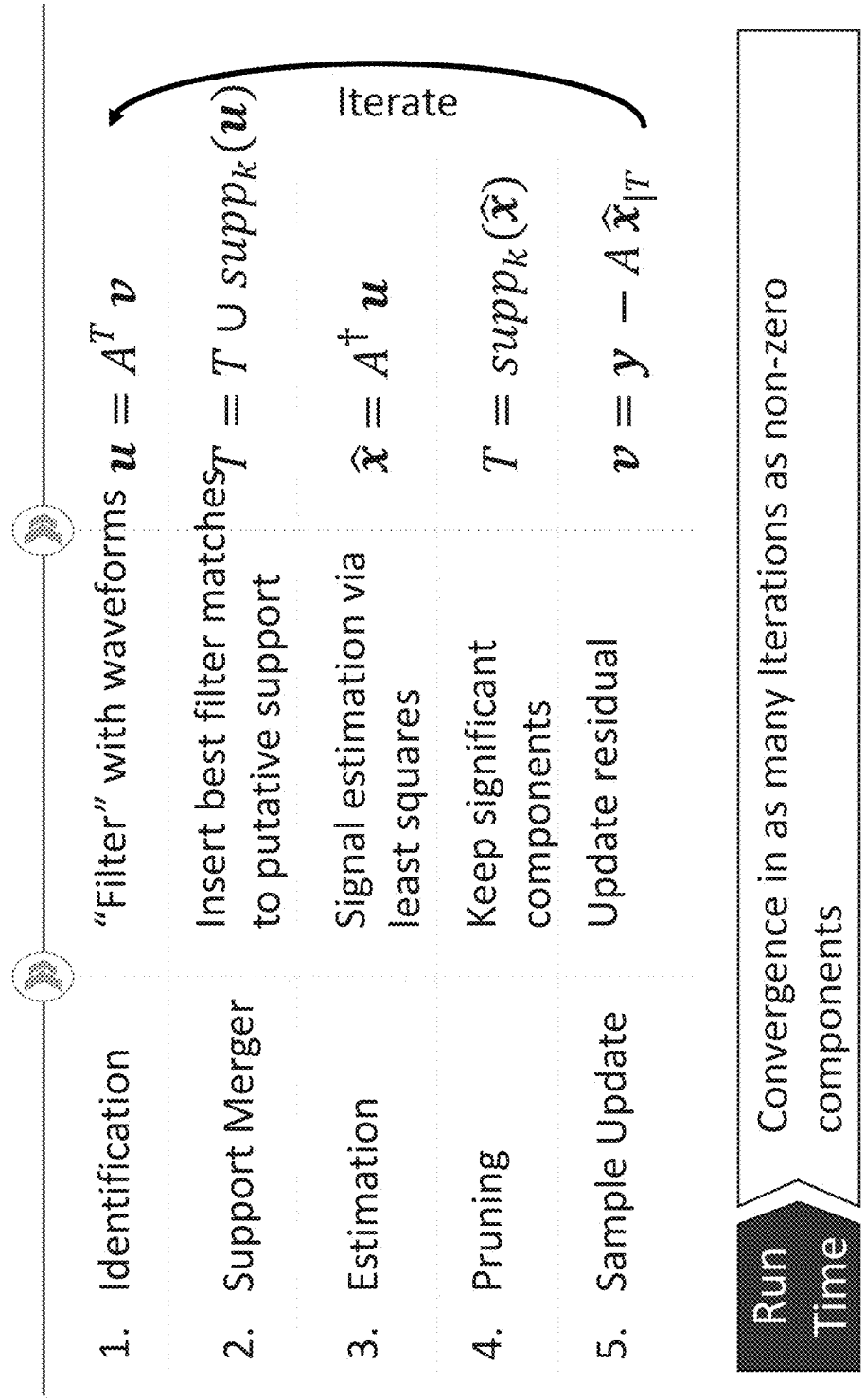
FIG. 5 conceptually illustrates a process for performing the CoSaMP method to recover spikes from multi-channel electrophysiological recordings in accordance with an embodiment of the invention.

For efficient sparse signal-recovery, systems and methods in accordance with many embodiments of the invention utilize the popular CoSaMP method described in Needell, Deanna, and Joel A. Tropp. "CoSaMP: Iterative signal recovery from incomplete and inac-curate samples." Applied and computational harmonic analysis 26.3 (2009): 301-321, the disclosure of which including (but not limited to) the discussion of the CoSaMP method is incorporated by reference herein in its entirety. An overview of the manner in which the CoSaMP method can be utilized in the context of multi-channel electrophysiological recordings is conceptually illustrated in FIG. 5.

To enable online application, the processing in the CoSaMP iterations is typically restricted to a finite buffer. Systems and methods in accordance with a number of embodiments of the invention remove elements from the buffer when the error-bound from Theorem 1 precludes the inclusion of old components in the selected component set. The necessary Eigenvalues are bounded using the spectrum of $A^TA$, which can be obtained during a training phase.

During online processing an uncertainty vector $\Delta b_t$ is maintained, based on the estimated maximum change from (13). For each putative spike event $x_{t,j}$ in the processing buffer the maximum achievable amplitude is bound by $x_{t,j}+\Delta b_{t,j}$. Let $\theta_{min}=\hat{x}_{t,j}-\Delta b_{t,j}$ with j such that it is the smallest amplitude of a selected element minus its uncertainty. The buffer in each iteration is shrunk to $_0$ if $x_{t,j}+\Delta b_{t,j}<\theta$ for all $t<t_0$. Meaning that if for all components of the processing buffer, the magnitude plus uncertainty is smaller than the smallest, selected component minus uncertainty, the buffer size is reduced.

To account for temporally homogeneous sparsity and signal distribution, the number of components to be selected by CoSaMP can be defined per temporal slice, meaning new components are added when new data is acquired.

While various processes for performing online spike recovery from multi-channel electrophysiological recordings are described above with respect to FIG. 5 in the context of various implementations of the CoSaMP method, any of a variety of alternative implementations of the CoSaMP method and/or other processes for sparse signal recovery can be implemented that utilize knowledge of a buffer size or time window over which to process recorded data obtained using Theorem 1 to detect spikes during online processing as appropriate to the requirements of specific applications in accordance with various embodiments of the invention. Performance of systems for performing online spike recovery from multi-channel electrophysiological recordings in accordance with a number of embodiments of the invention is discussed below with reference to a simulated data set and multi-channel electrophysiological recordings made in the visual cortex of a behaving macaque monkey. Additional analysis of results obtained using the system and methods described herein can be found in U.S. Provisional Application Ser. No. 62/816,783 incorporated by reference in its entirety above.

Simulations

For the simulations test data was generated using waveform templates from recordings in area V4 of the macaque visual cortex. The templates were extracted as the average single-unit activity from manual spike sorting. To compare the different bounds on the error propagation n=250 random encoding matrices were generated, using six Poisson spike trains with a firing rate randomly chosen between 10 Hz and 100 Hz. The high number of neurons was chosen to promote activity overlap in order to better depict the decay of the bounds. Three bounds were compared to the actual magnitude of the off-diagonal entries: 1) The bound based on DMS, 2) the same bound assuming a reduced bandwidth based on the refractory period and 3) the bound based on the effective bandwidth from Lemma 2. For each random encoding matrix the bounds were calculated for the 100 off-diagonal elements with the largest ground-truth magnitude and stored in a vector sorted by the ground-truth magnitude. The mean and standard-error of this vector was studied across the random trials. To test the robustness of the proposed online processing, Gaussian noise was retrospectively added to Poisson spike trains of two neurons (30 Hz and 70 Hz) to achieve a signal-to-noise ratio (SNR) of 2-15. n=100 random signal traces of 100 ms length were generated for each SNR. CoSaMP with online processing was compared to batch processing, in terms of identified spiking events and amplitude. Furthermore, the error rate, defined as % missed spikes compared to the ground truth, was studied for online processing at each SNR.

Simulation Results

Figures 6A, 6B, 6C:
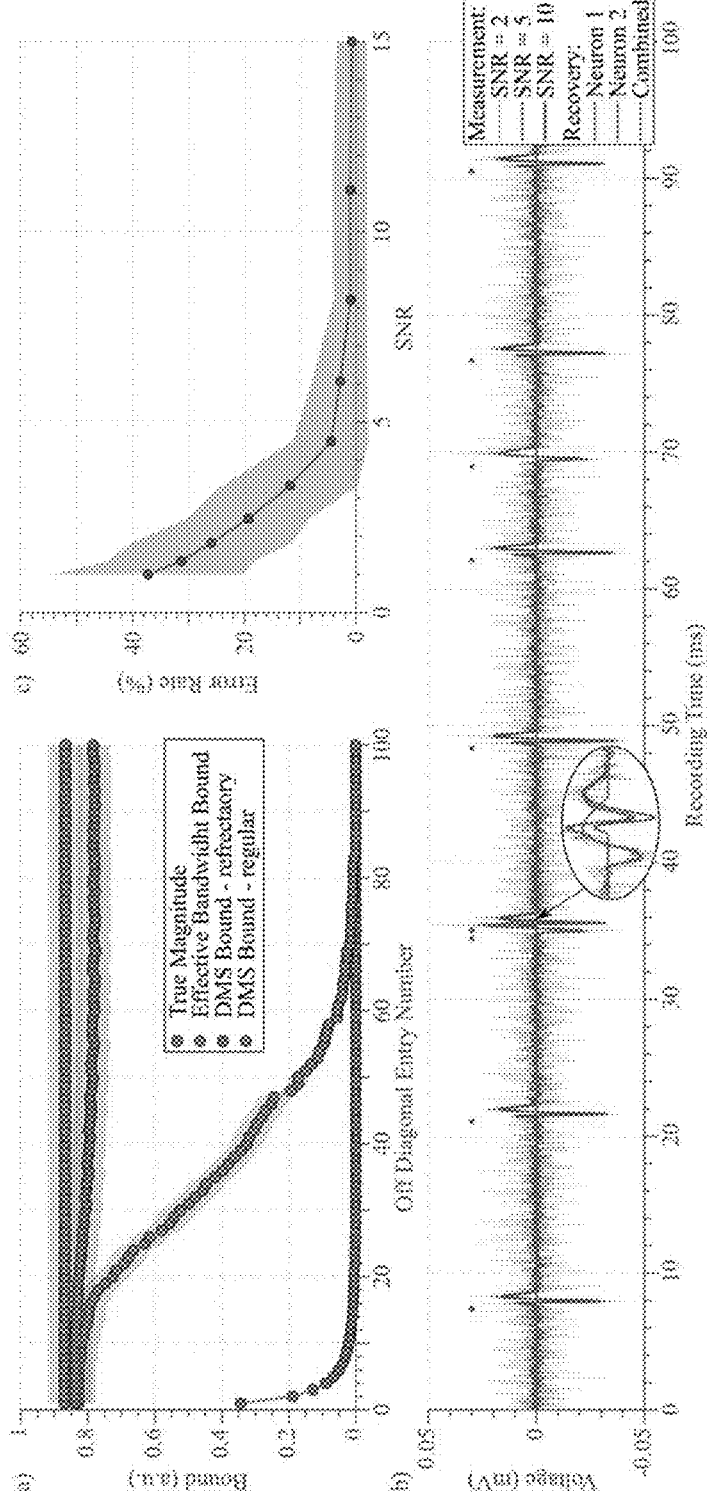
FIGS. 6A-6C illustrate results of application of processes in accordance with various embodiments of the invention to spike recovery from simulated data generated using waveform templates from recordings in area V4 of the macaque visual cortex.

In simulations using multiple random encoding matrices the effective bandwidth provides a more restrictive bound than DMS, even when using the refractory period assumption (FIG. 6A). The differences are most pronounced for lower magnitude off-diagonals, where the encoding matrix can be better decoupled. The spike train excerpt in FIG. 6B shows an example where a process in accordance with an embodiment of the invention successfully resolves overlapping activity despite substantial noise (SNR=5). FIG. 6B illustrates a representative spike train at three SNR levels, showing the identified spiking activity using online spike recovery at SNR=5. Ticks indicate the identified spike times and the magnification highlights a resolution of an overlapping spike. No difference for the identified spike times was found between online and batch processing, verifying the validity of the derived buffer sizes. The average relative deviation of the recovered magnitudes was in the order of machine precision ($9.29 \cdot 10^{-17} \pm 2.04 \ 10^{-16}$). FIG. 6C shows the error rates for the proposed online processing at different SNR values, indicating negligible errors for SNR>7. The error rate increases beyond 10% for SNR<4.

In-Vivo Experiments

Electrophysiology data was recorded in the visual cortex of a behaving macaque monkey using a 32 channel S-probe (Plexon Inc, Dallas. USA) with 50 μm electrode spacing. Four adjacent channels displaying the highest activity were selected for further analysis. Two isolated cells were identifiable from the data in channel-by-channel spike sorting. Based on correlogram analysis, multi-channel templates were formed from the channel-by-channel spike sorting and used for online spike recovery using processes similar to those described above. Spike times as obtained with the proposed method were compared to conventional sorting.

In-Vivo Results

Figures 7A, 7B:
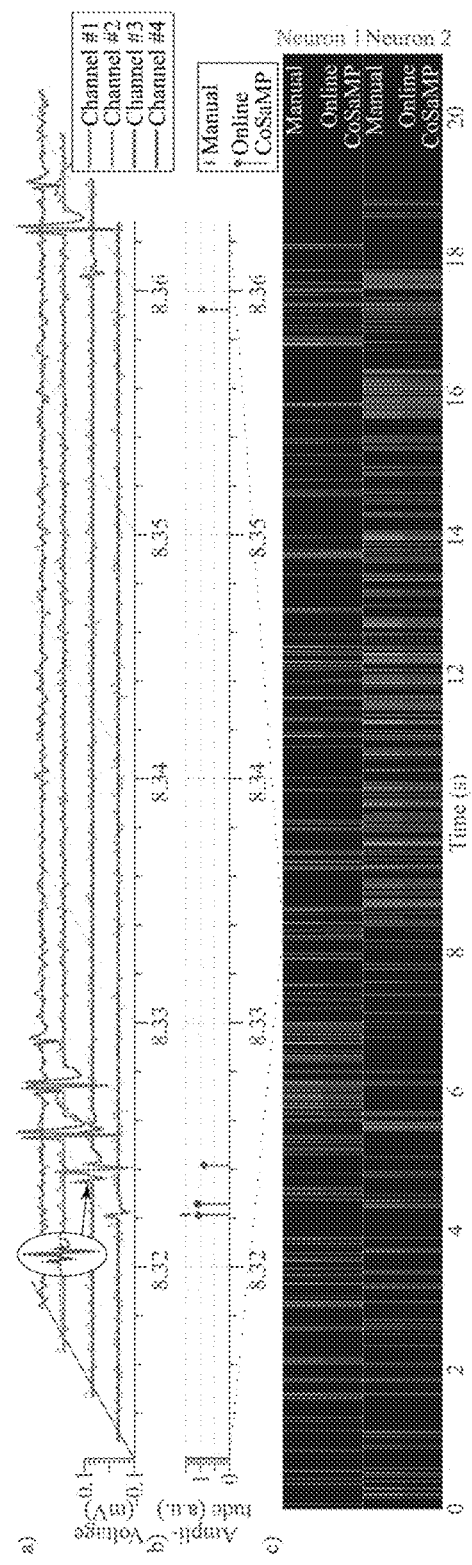
FIGS. 7A and 7B illustrate results of application of processes in accordance with various embodiments of the invention to spike recovery from 32-channel electrophysiological recordings obtained from a behaving macaque monkey.

The spiking activity identified by manual spike sorting of high-density multi-channel data compared with the activity identified with the proposed online algorithm shows excellent agreement in the raster plot shown in FIGS. 7A and 7B. For neuron 1 the proposed online algorithm identified all 235 spiking events from manual spike sorting and 18 additional events (deviation: 7.66%). For neuron 2 18 events of the 347 identified with manual sorting were not picked up, and 5 events were added (deviation: 6.63%). However, due to the lack of overlap-resolution manual spike sorting performed suboptimally as illustrated in FIGS. 7A and 7B. Only one of the overlapping spikes at 8.32 s was recognized in manual spike sorting, burying the concurrent activity of the other neuron. Both events were resolved with the proposed algorithm. Note that this can be of crucial importance for analysis of synchrony or correlation of activity. Although results are presented herein with respect to electrophysiology data recorded using a 32 channel S-probe, online spike recovery processes can be performed by recording systems similar to those described above with reference to FIG. 2 utilizing any of a variety of probes having less than or more than 32 channels as appropriate to the requirements of specific applications in accordance with various embodiments of the invention. Furthermore, such recording systems can be utilized to perform online spike recovery with respect to electrophysiology data recorded with respect to any of a variety of neural tissue types in any of number of different species.

Although the present invention has been described in certain specific aspects, many additional modifications and variations would be apparent to those skilled in the art. It is therefore to be understood that the present invention can be practiced otherwise than specifically described including in the context of greedy methods other than the CoSaMP method for performing sparse signal recovery without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method of performing online spike recovery from multi-channel electrophysiological recordings, comprising:
   determining a set of waveform templates;
   continuously obtaining multi-channel electrophysiological recordings using a multi-channel electrode; and
   automatically performing online spike recovery from the multi-channel electrophysiological recordings to identify spike activity using a processing system that performs a method for sparse signal recovery that continuously adjusts a processing buffer size based upon newly obtained multi-channel electrophysiological recordings, wherein the processing buffer comprises a plurality of components, and wherein the processing systems adjusts the buffer size based on a magnitude value of the plurality of components.

2. The method of claim 1, wherein the waveform templates are determined using offline waveform extraction from a set of training data.

3. The method of claim 1, wherein the waveform templates are updated over time.

4. The method of claim 1, wherein the processing system outputs information identifying spike activity detected by the processing system during the online spike recovery.

5. The method of claim 4, wherein the information describing the identified spike activity comprises temporal and spatial location information.

6. The method of claim 1, further comprising generating control signals for a stimulus provided to a subject monitored by the multi-channel electrode in response to the identified spiking activity using the processing system.

7. The method of claim 1, further comprising generating control signals for a device in response to the identified spiking activity using the processing system.

8. The method of claim 1, wherein the processing system adjusts the buffer size based upon an effective bandwidth determination.

9. The method of claim 1, wherein the method for sparse signal recovery performed by the processing system is a Compressive Sampling Matching Pursuit (CoSaMP) process.

10. The method of claim 1, wherein the processing system adds new components to the processing buffer when new multi-channel electrophysiological recordings are obtained.

11. The method of claim 1, wherein the processing system maintains an uncertainty vector for each component in the processing buffer and when, for a sequence of components of the processing buffer, the magnitude plus uncertainty is smaller than the magnitude of a component selected as a spike event minus the selected component's uncertainty, the processing system removes the sequence of components from the processing buffer and reduces the size of the processing buffer.

12. The method of claim 1, wherein automatically performing online spike recovery from the multi-channel electrophysiological recordings to identify spiking activity using the processing system further comprises:
   buffering an initial component set including at least one putative spike event in the processing buffer;
   receiving new multi-channel electrophysiological recordings and adding at least one new component to the processing buffer;
   estimating uncertainty for components in the initial component set stored in the processing buffer including the at least one putative spike event;
   removing from the processing buffer components of the buffered initial component set occurring prior to a putative spike event, when the estimated uncertainty of each of the components prior to the putative spike event is less than an uncertainty threshold; and decreasing the buffer length of the processing buffer based upon the components removed from the buffer.

13. The method of claim 1, wherein the multi-channel electrode comprises at least 32 channels.

14. A multi-channel electrophysiological recording system, comprising:
a probe capable of capturing multi-channel electrophysiological recordings; and
a processor system configured by a software application to:
determine a set of waveform templates;
obtain new multi-channel electrophysiological recordings using the probe; and
when new multi-channel electrophysiological recordings are obtained:
add at least one new component to a processing buffer comprising a plurality of components, where the at least one new component is determined using the waveform templates;
adjust the processing buffer size based on a magnitude value of the plurality of components; and
perform online spike recovery by identifying spike events using the components in the processing buffer.

15. The recording system of claim 14, wherein the processor system is further configured by the software to determine the waveform templates using offline waveform extraction from a set of training data.

16. The recording system of claim 14, wherein the processor system is further configured by the software to update the waveform templates over time.

17. The recording system of claim 14, wherein the processor system is further configured by the software to output information describing the identified spiking activity.

18. The recording system of claim 17, wherein the information describing the identified spiking activity comprises temporal and spatial location information.

19. The recording system of claim 14, further comprising an output interface, wherein the processor system is further configured by the software to control a device in response to the identified spiking activity via the output interface.

20. The recording system of claim 14, further comprising an output interface, wherein the processor system is further configured by the software to control stimuli provided to a subject monitored by the probe in response to the identified spiking activity via the output interface.

21. The recording system of claim 14, further comprising an analog-to-digital converter configured to receive signals from the probe and store data in a memory of the processor system.

22. The recording system of claim 14, wherein the processor system is further configured by the software to adjust the buffer size based upon an effective bandwidth determination.

23. The recording system of claim 14, wherein the processor system is further configured by the software to perform online spike recovery using a sparse signal recovery processing utilizing Compressive Sampling Matching Pursuit (CoSaMP).

24. The recording system of claim 14, wherein the processor system is further configured by the software to:
maintain an uncertainty vector for each component in the processing buffer; and
remove a sequence of components from the processing buffer and reduce the size of the processing buffer, when the sequence of components each have a magnitude plus uncertainty that is smaller than the magnitude of a component selected as a spike event minus the selected component's uncertainty.

25. The recording system of claim 14, wherein the processor system is further configured by the software to perform online spike recovery by:
buffering an initial component set including at least one putative spike event in the processing buffer configured to have an initial buffer length;
estimating uncertainty for components in the initial component set stored in the processing buffer including the at least one putative spike event;
removing from the processing buffer components of the buffered initial component set occurring prior to a putative spike event, when the estimated uncertainty of each of the components prior to the putative spike event is less than an uncertainty threshold; and
decreasing the buffer length of the processing buffer based upon the components removed from the buffer.

26. The recording system of claim 14, wherein the multi-channel electrode comprises at least 32 channels.

* * * * *